(12) United States Patent
Besko

(10) Patent No.: US 8,818,476 B2
(45) Date of Patent: Aug. 26, 2014

(54) REFLECTANCE AND/OR TRANSMISSIVE PULSE OXIMETER

(71) Applicant: Nellcor Puritan Bennett LLC, Boulder, CO (US)

(72) Inventor: David P. Besko, Thorton, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/650,788

(22) Filed: Oct. 12, 2012

(65) Prior Publication Data

US 2013/0035562 A1 Feb. 7, 2013

Related U.S. Application Data

(62) Division of application No. 12/495,551, filed on Jun. 30, 2009, now Pat. No. 8,311,601.

(51) Int. Cl.
*A61B 5/1455* (2006.01)
(52) U.S. Cl.
USPC .................. 600/344; 600/323; 600/310
(58) Field of Classification Search
USPC .................................... 600/310–344
See application file for complete search history.

(56) References Cited

U.S. PATENT DOCUMENTS

| | | | |
|---|---|---|---|
| 5,361,758 A | 11/1994 | Hall et al. | |
| 5,507,286 A | 4/1996 | Solenberger | |
| 5,673,693 A | 10/1997 | Solenberger | |
| 5,830,136 A | 11/1998 | Delonzor | |
| 5,910,108 A | 6/1999 | Solenberger | |
| 6,018,673 A | 1/2000 | Chin et al. | |
| 6,377,829 B1 | 4/2002 | Al-Ali | |
| 6,470,199 B1 | 10/2002 | Kopotic et al. | |
| 6,553,243 B2 | 4/2003 | Gurley | |
| 6,622,034 B1 | 9/2003 | Gorski et al. | |
| 6,671,531 B2 | 12/2003 | Al-Ali et al. | |
| 6,681,126 B2 | 1/2004 | Solenberger | |
| 6,725,075 B2 | 4/2004 | Al-Ali | |
| 6,731,963 B2 | 5/2004 | Finarov et al. | |
| 6,950,687 B2 | 9/2005 | Al-Ali | |
| 7,024,235 B2 | 4/2006 | Melker et al. | |
| 7,039,449 B2 | 5/2006 | Al-Ali | |
| 7,113,815 B2 | 9/2006 | O'Neil et al. | |
| 7,127,278 B2 | 10/2006 | Melker et al. | |
| 7,132,641 B2 | 11/2006 | Schulz et al. | |
| 7,190,986 B1 | 3/2007 | Hannula et al. | |
| 7,190,987 B2 | 3/2007 | Lindekugel et al. | |
| 7,209,774 B2 | 4/2007 | Baker | |
| 7,225,006 B2 | 5/2007 | Al-Ali et al. | |
| 7,272,425 B2 | 9/2007 | Al-Ali | |
| 7,292,150 B2 | 11/2007 | Shaw | |
| 7,305,262 B2 | 12/2007 | Brodnick et al. | |
| 7,423,526 B2 | 9/2008 | Despotis | |

(Continued)

FOREIGN PATENT DOCUMENTS

EP 724860 8/1996
EP 630203 7/2002

(Continued)

*Primary Examiner* — Eric Winakur
*Assistant Examiner* — Marjan Fardanesh
(74) *Attorney, Agent, or Firm* — Fletcher Yoder PC

(57) ABSTRACT

According to various embodiments, a medical sensor assembly may be configured to switch between transmission and reflectance mode. Such sensors may include multiple optical sensing components that may be activated or silent, depending on the mode in use. A practitioner may switch between modes based on the particular situation of the patient or based on the signal quality.

15 Claims, 9 Drawing Sheets

(56) References Cited

U.S. PATENT DOCUMENTS

| | | |
|---|---|---|
| 7,438,687 B2 | 10/2008 | Lewicke |
| 2003/0135099 A1 | 7/2003 | Al-Ali |
| 2003/0181799 A1 | 9/2003 | Lindekugel et al. |
| 2004/0133088 A1 | 7/2004 | Al-Ali |
| 2004/0147821 A1 | 7/2004 | Al-Ali et al. |
| 2006/0020179 A1 | 1/2006 | Anderson et al. |
| 2006/0036136 A1 | 2/2006 | Shaw |
| 2006/0200018 A1 | 9/2006 | Al-Ali |
| 2006/0217604 A1 | 9/2006 | Fein et al. |
| 2006/0276700 A1 | 12/2006 | O'Neil et al. |
| 2007/0027375 A1 | 2/2007 | Melker et al. |
| 2007/0142717 A1 | 6/2007 | Lowery et al. |
| 2007/0219440 A1 | 9/2007 | Hannula et al. |
| 2008/0030346 A1 | 2/2008 | Despotis |
| 2008/0033267 A1 | 2/2008 | Al-Ali |
| 2008/0076987 A1 | 3/2008 | Arizaga et al. |
| 2008/0221413 A1 | 9/2008 | Hoarau |
| 2008/0316488 A1 | 12/2008 | Mao et al. |

FOREIGN PATENT DOCUMENTS

| | | |
|---|---|---|
| EP | 1986543 | 11/2008 |
| WO | 9316629 | 9/1993 |
| WO | 2008019294 | 2/2008 |

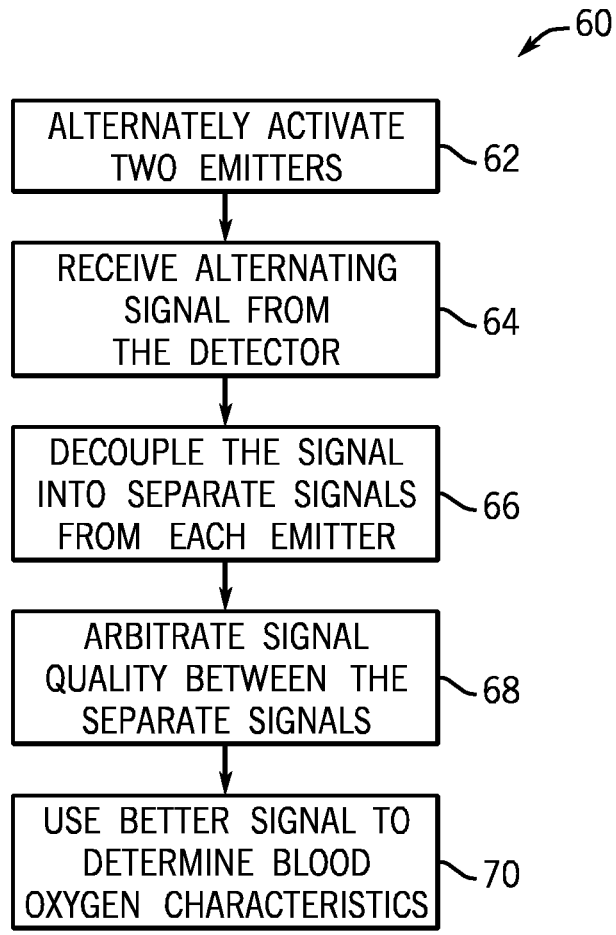
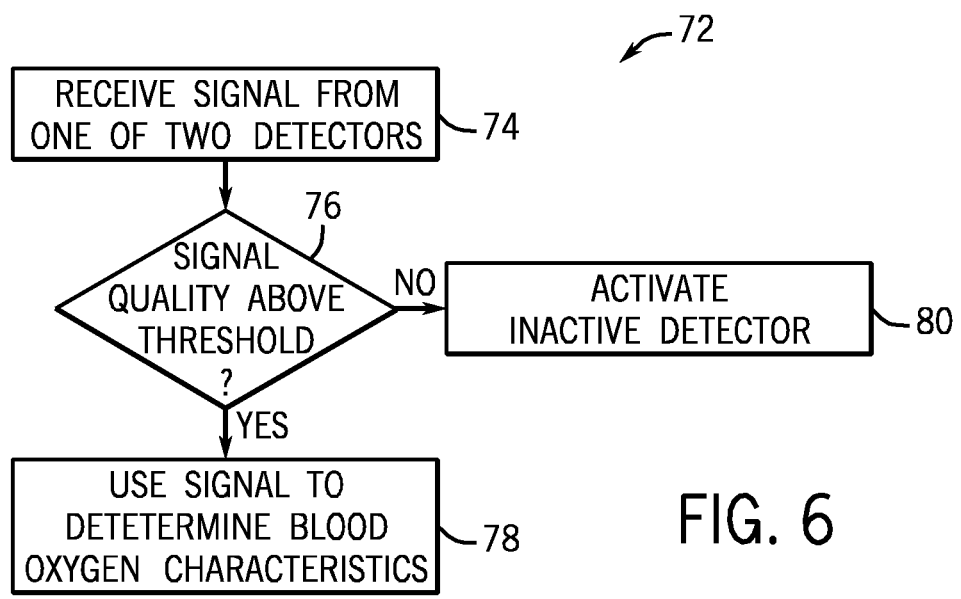

US 8,818,476 B2

REFLECTANCE AND/OR TRANSMISSIVE PULSE OXIMETER

CROSS-REFERENCE TO RELATED APPLICATIONS

This application is a divisional of U.S. application Ser. No. 12/495,551, filed Jun. 30, 2009, the disclosure of which is hereby incorporated by reference in its entirety.

BACKGROUND

The present disclosure relates generally to medical devices and, more particularly, to sensors used for sensing physiological parameters of a patient.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed and/or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms.

Pulse oximetry sensors may be applied to a patient's tissue site and secured, for example by adhesives, clips, or light pressure, to achieve a conforming fit. Some outside light infiltration into the sensor may be avoided by fitting the sensor snugly against the patient's tissue. However, such a conforming fit may be difficult to achieve over a range of patient physiologies without adjustment or excessive attention on the part of medical personnel. Further, patient movement may also interfere with the signal received from the sensor. For example, for the case a bandage-type sensor wrapped around the fingertip, if the finger is bent at a first joint, parts of the sensor may fold or buckle away from the tissue. Such small changes in the conformation of the sensor may cause the optical components to lose their contact with the skin, resulting in changes to the emitted and/or detected light, which in turn may lead to signal artifacts. While these artifacts may sometimes be addressed by signal processing and filtering to mitigate the effects, such signal processing may be complex.

BRIEF DESCRIPTION OF THE DRAWINGS

Advantages of the disclosure may become apparent upon reading the following detailed description and upon reference to the drawings in which:

FIG. 5 is a flow diagram of a method of selecting between transmission mode or reflectance mode for a two detector sensor according to an embodiment;

FIG. 6 illustrates a pulse oximetry system coupled to a multi-parameter patient monitor and a sensor according to an embodiment;

DETAILED DESCRIPTION OF SPECIFIC EMBODIMENTS

Figure 1:
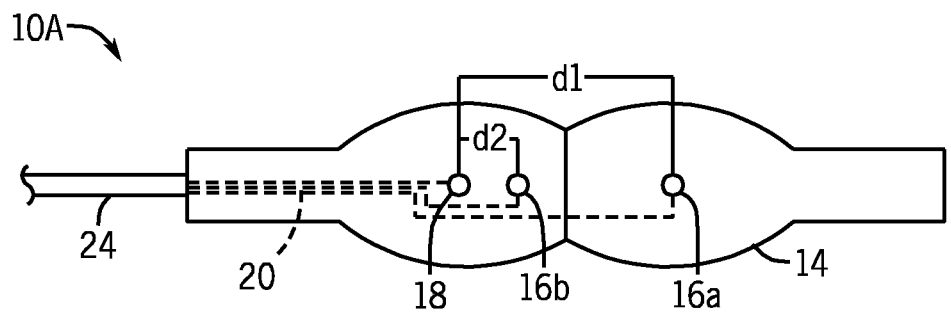
FIG. 1 is a perspective view of a dual-mode bandage-style sensor with two emitters according to an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical sensors such as pulse oximetry sensors may be placed on a patient in a location that is normally perfused with arterial blood to facilitate measurement of the desired blood characteristics, such as arterial oxygen saturation measurement ($SpO_2$). For example, common sensor sites include a patient's fingertips, toes, earlobes, or forehead. In addition, pulse oximetry sensors may be capable of performing intrauterine measurements. Sensors in either reflectance-type or transmission-type configurations (or, in certain cases, transflectance-type configurations) may be able to sense light that has been transmitted through the tissue.

Sensors as provided herein may be able to operate in both "transmission mode" and "reflectance mode." Transmission mode sensors include an emitter and detector that are typically placed on opposing sides of the sensor site. If the sensor site is a fingertip, for example, the sensor assembly is positioned over the patient's fingertip such that the emitter and detector lie on either side of the patient's nail bed. In other words, the sensor assembly is positioned so that the emitter is located on the patient's fingernail and the detector is located approximately 180° opposite the emitter on the patient's finger pad. During operation, the emitter shines one or more wavelengths of light through the patient's fingertip and the light received by the detector is processed to determine various physiological characteristics of the patient. In each of the embodiments discussed herein, it should be understood that the locations of the emitter and the detector may be exchanged. For example, the detector may be located at the top of the finger and the emitter may be located underneath the finger. In either arrangement, the sensor assembly will perform in substantially the same manner.

Reflectance mode sensors also operate by emitting light into the tissue and detecting the light that is transmitted and/or scattered by the tissue. However, reflectance type sensors include an emitter and detector that are typically placed on the same side of the sensor site. For example, a reflectance type sensor may be placed on a patient's fingertip or forehead such that the emitter and detector lie side-by-side. Reflectance type sensors detect light photons that are scattered back to the detector. Sensor assemblies may also be "transflectance," such as a sensor that may subtend a portion of a baby's heel.

Regardless of the placement of a sensor used for pulse oximetry, the reliability of the pulse oximetry measurement is related to the accurate detection of transmitted light that has passed through the perfused tissue and that has not been supplemented by undesired light sources or that has not been scattered or redirected before passing through the tissue and being detected. In addition, the reliability of the measurements may be affected by appropriate calibration of the received sensor signals to account for properties of the sensor and/or the sensing components. For example, reflectance-type sensors may be calibrated to account for the distance between the emitter and the detector on the sensor, which may influence the path length of the detected light. Transmission-type sensors may be calibrated to account for an estimated path length that reflects the width of the intended measurement site, such as a finger or an ear lobe. Accordingly, because sensors may be specifically calibrated for transmission use versus reflectance use, the quality of a sensor's measurements may be degraded if a transmission-type sensor is inadvertently used in a reflectance-type configuration.

As disclosed herein, sensors for pulse oximetry or other applications utilizing spectrophotometry are provided that may be capable of being used in both reflectance mode and transmission mode. Such sensors may provide distinct advantages for healthcare practitioners. Upon a decrease in signal quality, such dual-mode sensors may switch from reflectance mode to transmission mode or vice versa to improve the measured signal quality. For example, when a patient wearing a digit sensor taps a finger on a hard surface, the resultant signal artifacts may influence the signal from a reflectance mode sensor more profoundly, particularly if both the emitter and the detector, which are side-by-side, are directly tapped against the surface. By switching to transmission mode and activating a different detector on the opposing side of the sensor, the influence of the tapping motion on the signal may be decreased because, while the original emitter may still be directly affected by the tapping, the different detector on the opposing side of the sensor may be relatively shielded from the tapping motion. Further, switching modes may allow practitioners to sample different areas of the tissue to determine if a particular mode offers increased signal quality. For example, relatively small areas of tissue discoloration or low perfusion may be avoided by sampling both transmission mode and reflectance mode signal quality and selecting the highest quality signal.

FIG. 1 illustrates an example of a dual-mode bandage-type sensor 10A appropriate for use on a patient's digit. The sensor body 14 includes a transmission mode emitter 16a/detector 18 pair disposed on its surface. In addition, the sensor 10A also includes a second emitter 16b, which may pair with detector 18 in a reflectance mode arrangement. The sensor body 14 may include suitable electrical connectors, such as wire leads 20, that may operatively connect the emitters 16a and 16 and the detector 18 to a cable 24, which may be connected to a downstream monitoring device. The sensor 10A may also include an adhesive layer (not shown) in order to enhance the sensor's fit to the tissue.

The emitter 16a and detector 18 may be spaced apart on the sensor body 14 any suitable distance $d_1$ for a transmission-type arrangement. For example, the appropriate spacing $d_1$ may be 20-25 mm apart. In addition, the emitter 16 and the detector 18 may be spaced apart any suitable distance $d_2$ for a reflectance-type arrangement. In one embodiment, the distance $d_2$ may be 8-14 mm. As shown, emitter 16 is disposed between 16a and 18. However, it should be understood that emitter 16 may be located anywhere on the sensor body 14 such that the distance $d_2$ and configuration (e.g., the spacing and placement on the tissue) between 16 and 18 is appropriate for reflectance mode measurements.

Figure 2A:
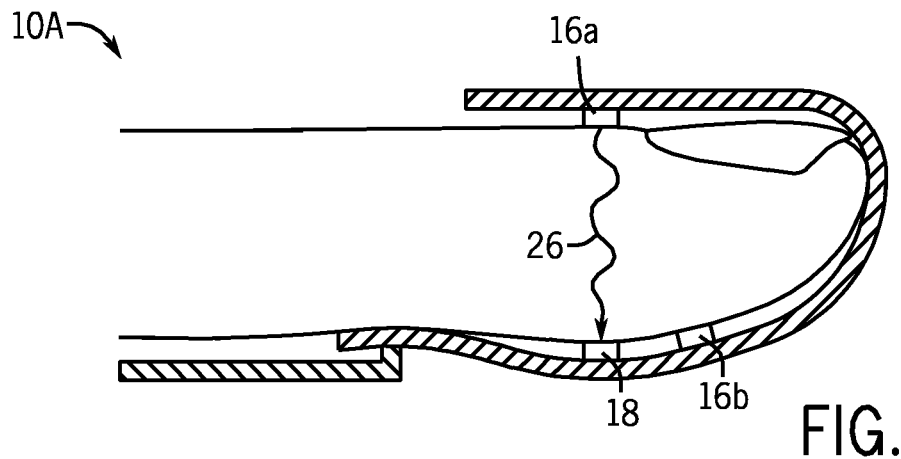
FIG. 2A is a side view of the sensor of FIG. 1 applied to a patient's digit and operating in transmission mode according to an embodiment.
Figure 2B:
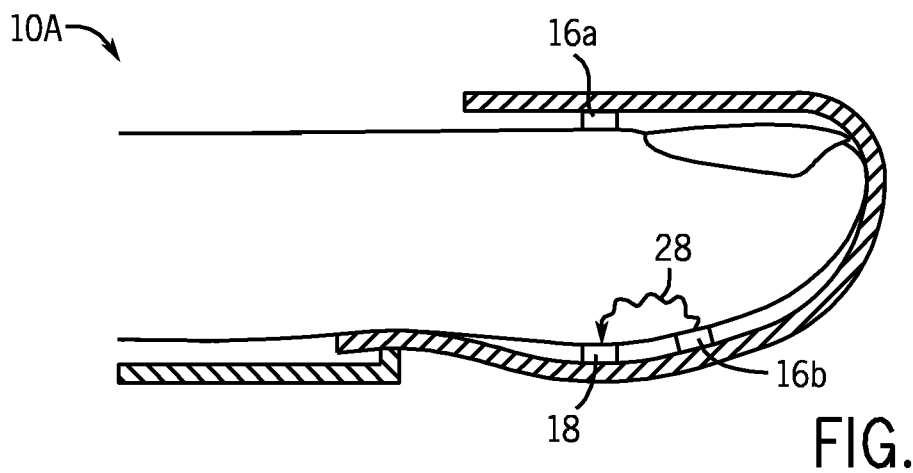
FIG. 2B is a side view of the sensor of FIG. 1 applied to a patient's digit and operating in reflectance mode according to an embodiment.

FIGS. 2A and 2B depict the sensor 10A applied to a patient's digit. FIG. 2A is a side view of sensor 10A operating in transmission mode, during which emitter 16a is active and emitter 16 is inactive. The light, depicted by arrow 26, emitted by emitter 16a travels through the tissue and is detected by detector 18. In FIG. 2B, the sensor 10A is shown operating in reflectance mode. In reflectance mode, a monitor or other device activates emitter 16 and not emitter 16a. The light 28 from emitter 16 is detected by the detector 18. As shown, the emitter 16 and the detector 18 may be arranged to be secured to the palmar side of the digit. Alternatively, the sensor 10A may be applied to the digit such that the emitter 16 and the detector 18 are secured to the nail side of the digit and the emitter 16a is applied on the palmar side.

Figure 3:
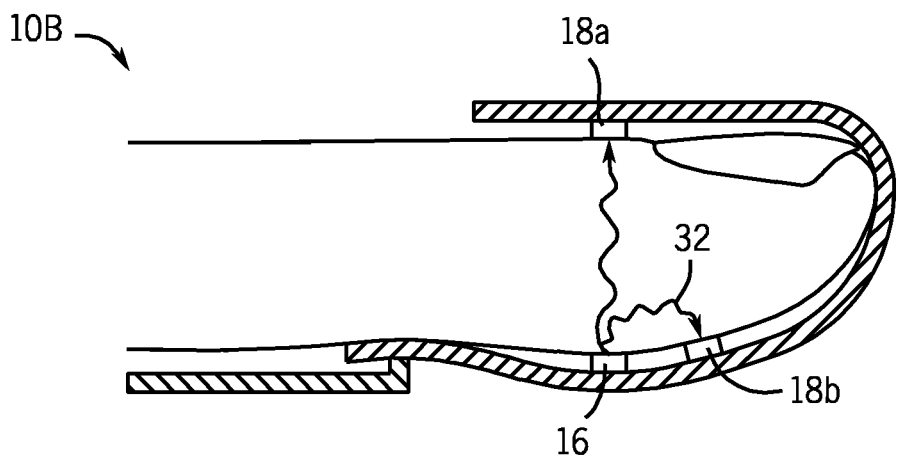
FIG. 3 is a side view of a dual-mode sensor with two detectors operating in reflectance mode and transmission mode simultaneously according to an embodiment.

In an alternative arrangement, a sensor may include multiple detectors 18 and a single emitter 16. As shown in FIG. 3, a sensor 10B may include an emitter 16 and detector 18a that are configured to operate in transmission mode in which light 30 from the emitter 16 travels through the tissue and encounters detector 18a. A second detector 18 may be configured to pair with emitter 16 in reflectance mode and detect light 32.

As shown, the transmission and reflectance modes may operate simultaneously. In other embodiments, the detectors 18*a* and 18 may be activated at different times.

As noted above, sensors 10 as provided herein may include one or more emitters paired with a single detector or one or more detectors paired with a single emitter. Regardless of the configuration of the optical sensing components, such sensors 10 may be able to switch between reflectance and transmission modes or, in embodiments, operate both modes simultaneously. As such, an upstream medical device may receive one signal from each emitter-detector pair or each "mode." These signals may be further processed to determine if a particular mode provides higher signal quality or is associated with fewer signal artifacts.

Figure 4:
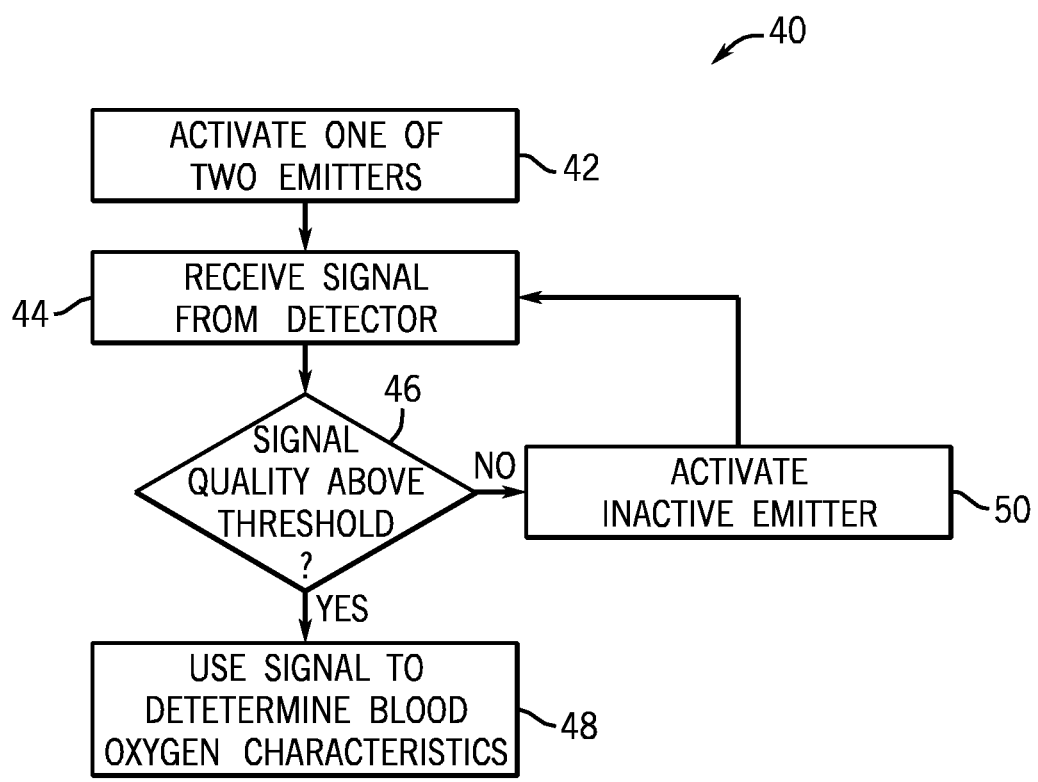
FIG. 4 is a flow diagram of a method of selecting between transmission mode or reflectance mode for a two emitter sensor according to an embodiment.

FIG. 4 is a flow diagram of a method 40 for processing sensor signals from both transmission and reflectance modes that may be used in conjunction with a sensor including multiple emitters, such as sensor 10A. At step 42, one of the two emitters 16 is activated, i.e., a drive signal is provided to the emitter from an upstream device. For certain types of sensors 10, a sensor may start out in a default mode, for example a transmission mode may be the default setting and the emitter 16*a* may be activated while emitter 16 is inactive. For other types of sensors 10, an operator may manually select a starting mode for operation, which may depend on the tissue site to be measured or other patient factors. At step 44, the signal from the detector 18 is received, for example by the upstream device, for processing. At step 46, any suitable processing method for determining signal quality may be employed to assess the quality of the received signal and to determine if the signal has attained a certain minimum threshold quality. In one embodiment, the signal quality may be assessed by performing a pulse qualification on the signal. In other embodiments, the signal quality may be assessed by determining a ratio of ratios for the signal. Such signal quality assessments may be performed as provided in U.S. Pat. No. 7,209,774, the specification of which is incorporated by reference herein in its entirety herein for all purposes. Other methods for determining signal quality may include detecting characteristic artifacts associated with certain types of patient or sensor movement.

If the signal of the default mode is determined to be of sufficient quality, the signal may then be used at step 48 to determine blood oxygen characteristics (or other physiological parameters), such as pulse rate and blood oxygen saturation. However, if the signal quality falls below a certain threshold, the inactive emitter 16, representing the "non-default" mode, may be activated at step 50. The signal from this emitter 16 may be received at step 46 and evaluated at step 48 for signal quality. If the signal quality from step 50 is above the threshold, then the sensor will continue to operate in the higher quality mode. If the signal quality from step 50 also falls below the quality threshold, then the device may prompt various alerts or error messages. The process 40 may be repeated to continuously or periodically assess the signal quality of the mode in use.

While the above method 40 may allow for switching modes between transmission and reflectance (or vice versa) only when an active mode falls below a certain quality, a sensor 10A may also provide alternating signals from both modes to an upstream device that may be continually arbitrated to determine the best quality signal, which may then be used to calculate blood oxygen characteristics. FIG. 5 is a flow diagram of a method 60 that may be used in conjunction with a sensor with two emitters, such as sensor 10A. At step 62, emitters 16*a* and 16 are alternately activated, such that when one is active, the other is inactive. The alternate activation may be one the order of microseconds or seconds and may be accomplished by a light drive input signal from a medical device as well as additional inputs or controls located on the sensor 10A and/or on the device, as discussed below (see FIGS. 10 and 11). The upstream medical device may receive the alternating signal (i.e., a signal that includes information from both emitters 16*a* and 16) from the detector 18 at step 64. At step 66, the signals may be decoupled into separate signals from each emitter 16*a* and 16, for example using timing information from a light drive and time processing unit. Alternatively, the signals may be decoupled using intensity information. For example, transmission mode signals may be generally about half the amplitude of reflectance mode signals because of the greater distance between the transmission mode emitter-detector pair.

Regardless of how the signals from each emitter 16 are separated, the separated signals may then be further processed at step 68 to determine signal quality. As discussed above, signal quality metrics may be measures of artifact contribution, pulse qualification or of a ratio-of-ratios calculation. The higher quality signal may be used in step 70 to determine blood oxygen characteristics. The signals from each emitter 16 may be continuously arbitrated such that the higher quality signal within a predetermined time window may be used.

As noted above, in addition to sensor configurations with two emitters, sensors 10 may include a single emitter 16 and two detectors 18 that may form both transmission-type and reflectance-type emitter-detector pairs. FIG. 6 is a flow diagram of a method 72 that may be used in conjunction with a sensor 10B. At step 74, one of the two detectors 18 is activated, i.e., the incoming signal is received and accessed for further processing at an upstream medical device. The sensor 10B may start out in a default mode, for example a transmission mode may be the default setting and the detector 18*a* may be activated while detector 18 is inactive, or the default mode may be input by an operator. At step 76, any suitable processing method for determining signal quality may be employed to assess the quality of the received signal from the active detector 18 and to determine if the signal has attained a certain minimum threshold quality. If the signal of the default mode is determined to be of sufficient quality, the signal may then be used at step 78 to determine blood oxygen characteristics. However, if the signal quality falls below a certain threshold, the inactive detector 18, representing the "non-default" mode, may be activated at step 80, and the signal from this detector may be further processed to determine its signal quality.

Figure 7:
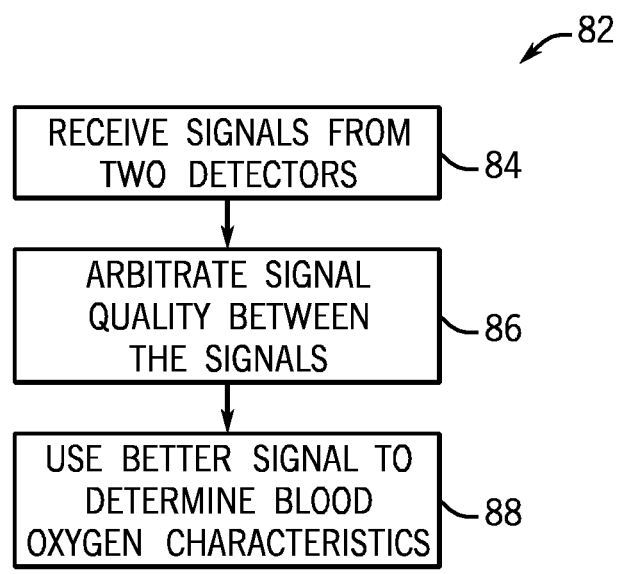
FIG. 7 is a block diagram of a pulse oximetry system according to an embodiment.

In one embodiment, a sensor 10B may operate transmission mode and reflectance mode simultaneously (see FIG. 3). In such an embodiment, detectors 18*a* and 18 may receive light concurrently from emitter 16. FIG. 7 is a flow diagram of a method 82 that may be used in conjunction with a sensor 10B during either simultaneous operation of both detectors 18*a* and 18 or, in embodiments, alternate operation of both detectors 18. At step 84, incoming signals from detectors 18*a* and 18 are received and accessed for further processing at an upstream medical device. Signal quality of both detector signals may be assessed by any suitable method at step 86 and the signal quality may be arbitrated. At step 88, the higher quality signal may be used to determine blood oxygen characteristics.

Figure 8:
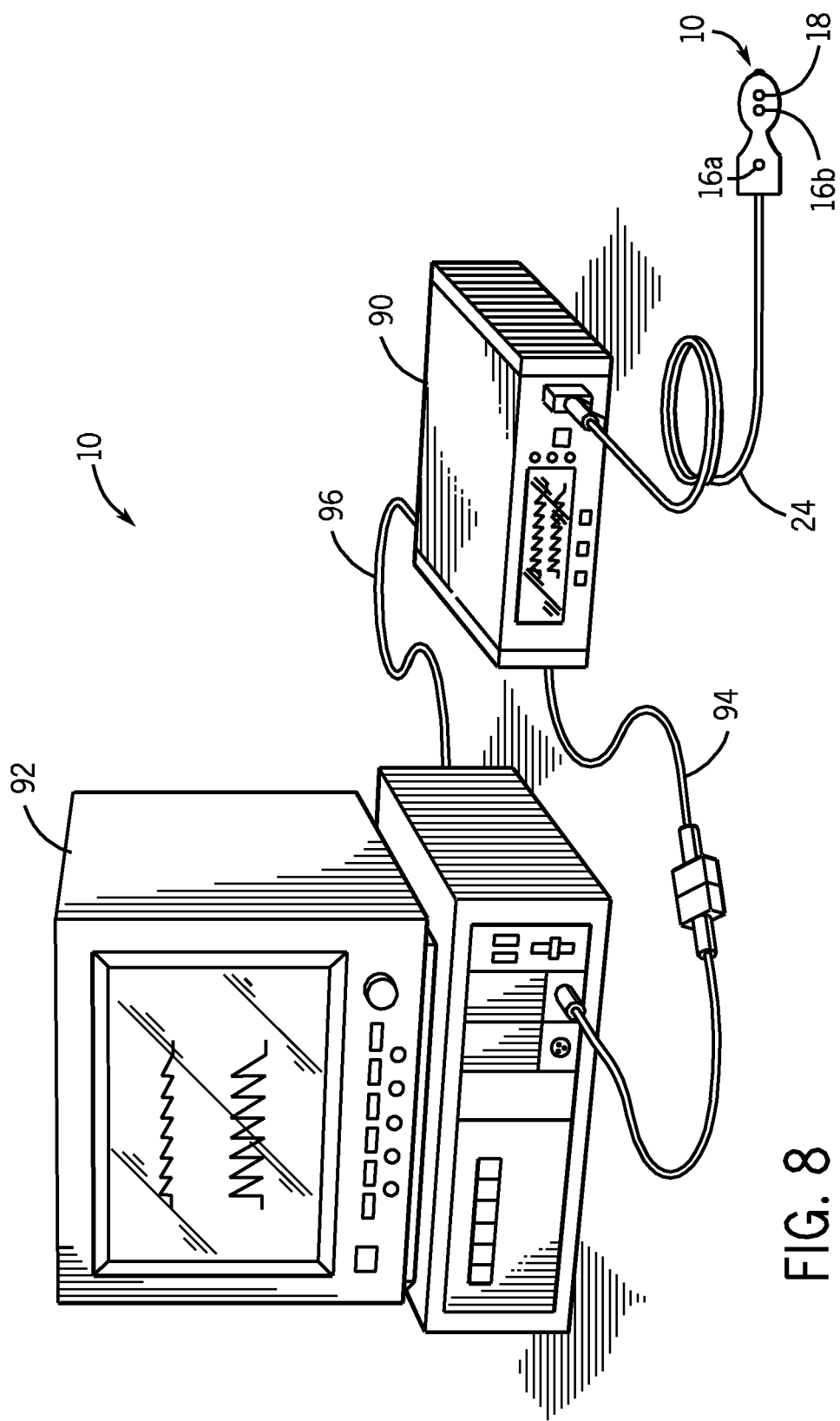
FIG. 8 is a block diagram of a dual-mode sensor with two emitters and a control on the monitor for switching between the two emitters according to an embodiment.

A sensor or sensor assembly, illustrated generically as a sensor assembly 10, may be used in conjunction with a pulse oximetry monitor 90, as illustrated in FIG. 8. It should be appreciated that the cable 24 of the sensor assembly 10 may be coupled to the monitor 90 or it may be coupled to a transmission device to facilitate wireless transmission between the sensor assembly 10 and the monitor 90. The monitor 90 may be any suitable pulse oximeter, such as those available from Nellcor Puritan Bennett LLC. Furthermore, to upgrade conventional pulse oximetry provided by the monitor 90 to provide additional functions, the monitor 90 may be coupled to a multi-parameter patient monitor 92 via a cable 94 connected to a sensor input port or via a cable 96 connected to a digital communication port.

Figure 9:
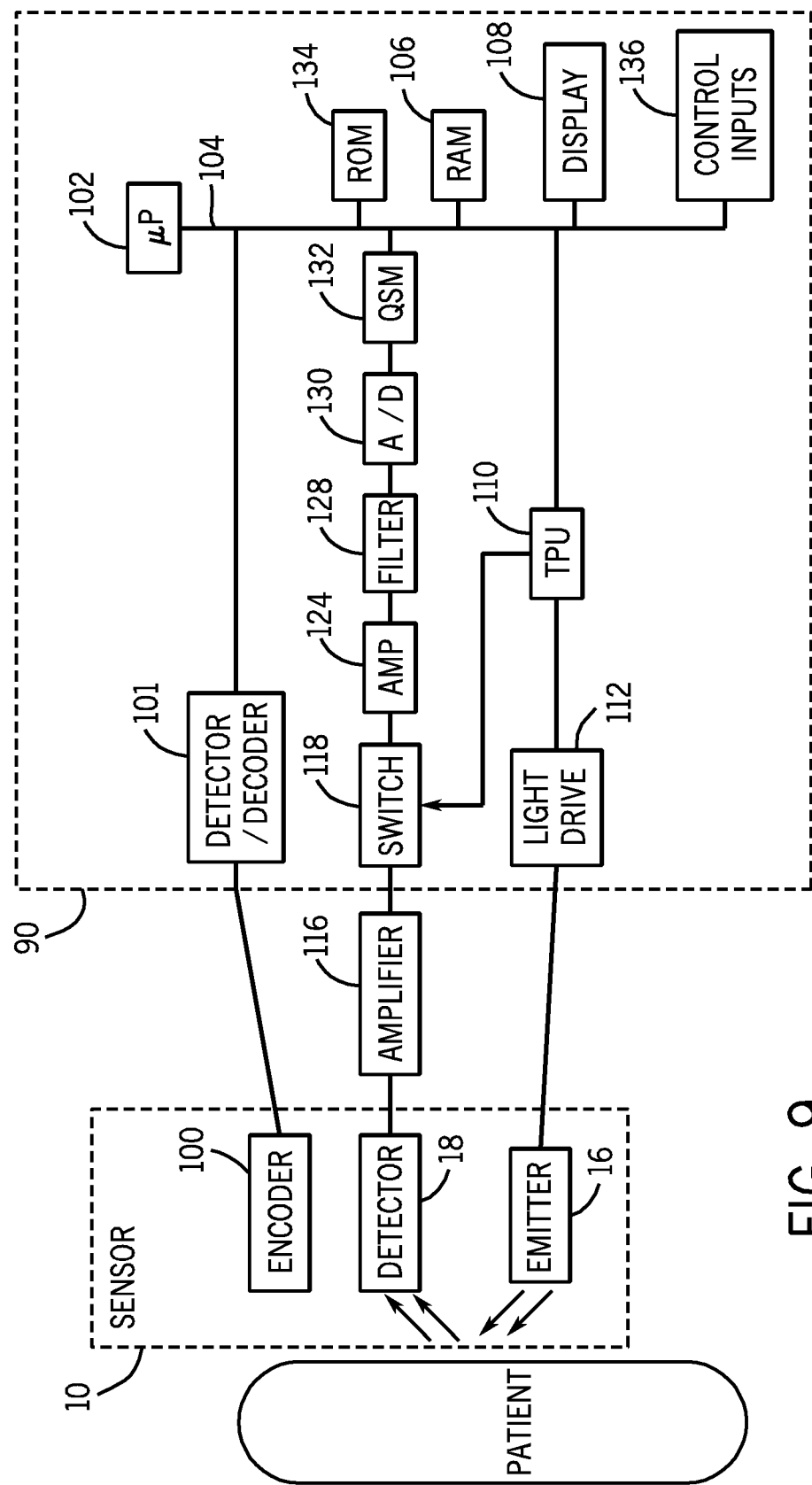
FIG. 9 is a block diagram of a dual-mode sensor with two emitters and a control on the sensor for switching between the two emitters according to an embodiment.

FIG. 9 is a block diagram of an embodiment of a pulse oximeter 90 that may be configured to implement the embodiments of the present disclosure. Light from one or more emitters 16 may pass into a blood perfused tissue, and may be scattered, and then detected by one or more detectors 18. An example of a sensor assembly 10 containing at least one emitter 16 and at least one detector 18 may also contain an encoder 100 which may be capable of providing signals indicative of the wavelength(s) of light source 16 to allow the oximeter to select appropriate calibration coefficients for calculating oxygen saturation. The encoder 100 may, in an embodiment, be a resistor.

In an embodiment, the sensor assembly 10 may be connected to a pulse oximetry monitor 90. The monitor 90 may include a microprocessor 102 coupled to an internal bus 104. Also connected to the bus may be a RAM memory 106 and a display 108. A time processing unit (TPU) 110 may provide timing control signals to light drive circuitry 112, which controls when the emitter 16 is activated, and if multiple light sources are used, the multiplexed timing for the different light sources. TPU 114 may also control the gating-in of signals from detector 18 through an amplifier 116 and a switching circuit 118. These signals are sampled at the proper time, depending at least in part upon which of multiple light sources is activated, if multiple light sources are used. The received signal from the detector 18 may be passed through an amplifier 124, a low pass filter 128, and an analog-to-digital converter 130. The digital data may then be stored in a queued serial module (QSM) 132, for later downloading to RAM 106 or ROM 134 as QSM 132 fills up.

In an embodiment, based at least in part upon the received signals corresponding to the light received by detector 18, microprocessor 102 may calculate the oxygen saturation using various algorithms. These algorithms may require coefficients, which may be empirically determined, and may correspond to the wavelengths of light used. The algorithms may be stored in a ROM 134 and accessed and operated according to microprocessor 102 instructions. For example, the encoder 100 may communicate with decoder 101 to allow the microprocessor 102 to determine the appropriate coefficients.

In an embodiment of a two-wavelength system, the particular set of coefficients chosen for any pair of wavelength spectra may be determined by a value indicated by the encoder 100 corresponding to a particular light source and particular emitter-detector separation distances in a particular sensor assembly 10. In one embodiment, multiple resistor values may be assigned to select different sets of coefficients, or the sets of coefficients may be stored on a digital medium. In another embodiment, the resistors are used to select from among the coefficients appropriate for an infrared source paired with either a near red source or far red source. The selection between whether the near red or far red set will be chosen can be selected with a control input from control inputs 136. Control inputs 136 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The sensor assembly 10 includes at least one emitter 16 and at least one detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

For pulse oximetry applications, the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 16 and the detector 18 may be disposed on a sensor body, which may be made of any suitable material, such as plastic, foam, woven material, or paper. Alternatively, the emitter 16 and the detector 18 may be remotely located and optically coupled to the sensor assembly 10 using optical fibers. In the depicted embodiments, the sensor assembly 10 is coupled to a cable 24 that is responsible for transmitting electrical and/or optical signals to and from the emitter 16 and detector 18 of the sensor assembly 10. The cable may be permanently coupled to the sensor assembly 10, or it may be removably coupled to the sensor assembly 10—the latter alternative being more useful and cost efficient in situations where the sensor assembly 10 is disposable.

Figure 10:
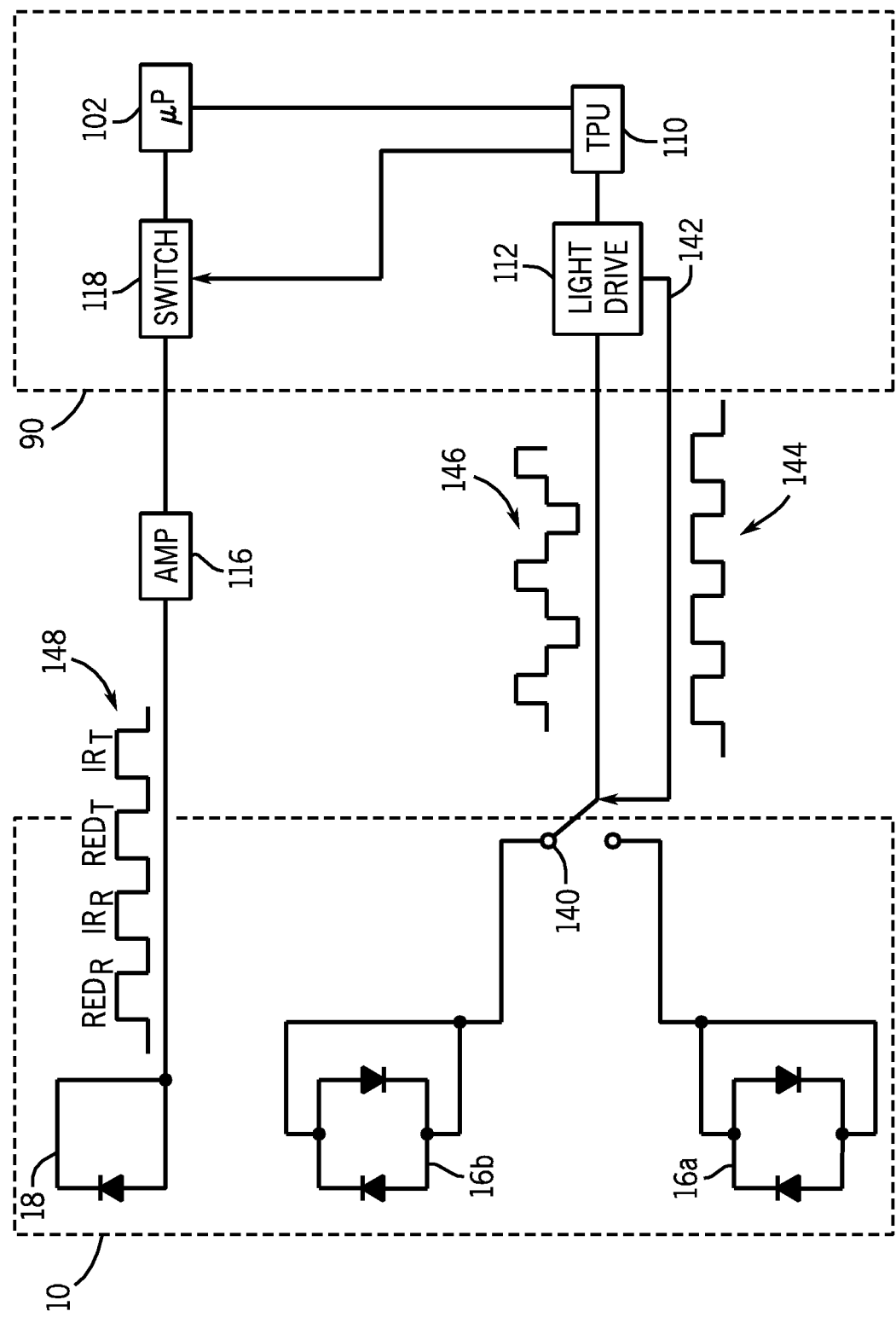
FIG. 10 is a block diagram of a dual-mode sensor with two emitters and a control on the monitor for activating each emitter according to an embodiment.

Depending on the particular configuration of the sensor 10, the sensor 10 and/or the monitor 90 may include certain devices for controlling the activation of either two separate emitters 16 or two separate detectors 18. As shown in FIG. 10, a monitor 90 may provide an input signal 142 to a switch 140 that controls switching between emitter 16a and emitter 16. As shown, switch 140 may be a hardware switch located on the sensor 10. In other embodiments, the switch 140 may be associated with cable 20 or may be located in the monitor 90. The input signal 142 may be generated by light drive 112 and, as shown, may be an alternating signal 144 that causes the sensor 10 to periodically switch between emitter 16a and emitter 16. It should be understood that the shape of signal 144 may be changed as desired or according to various inputs from microprocessor 102 (e.g., signal quality inputs) to provide different activation times for each emitter 16. For example, the signal 144 may activate only emitter 16a or only emitter 16 until signal quality from the active emitter 16 deteriorates. Light drive 112 may also generate a drive signal 146 to alternately drive a red and IR photodiode pair for the active emitter 16. The detector signal 148 includes both the red and IR components from the active emitter 16. When emitter 16a and emitter 16 are alternately activated, the detector signal 148 received at switch 118 may include a $Red_R$ portion (red reflectance), an $IR_R$ portion (IR reflectance), a $Red_T$ portion (red transmission) and an $IR_T$ portion (IR transmission). Input from the time processing unit 110 may be used to assign parts of the signal to the appropriate emitter-detector pair (e.g., reflectance or transmission).

Figure 11:
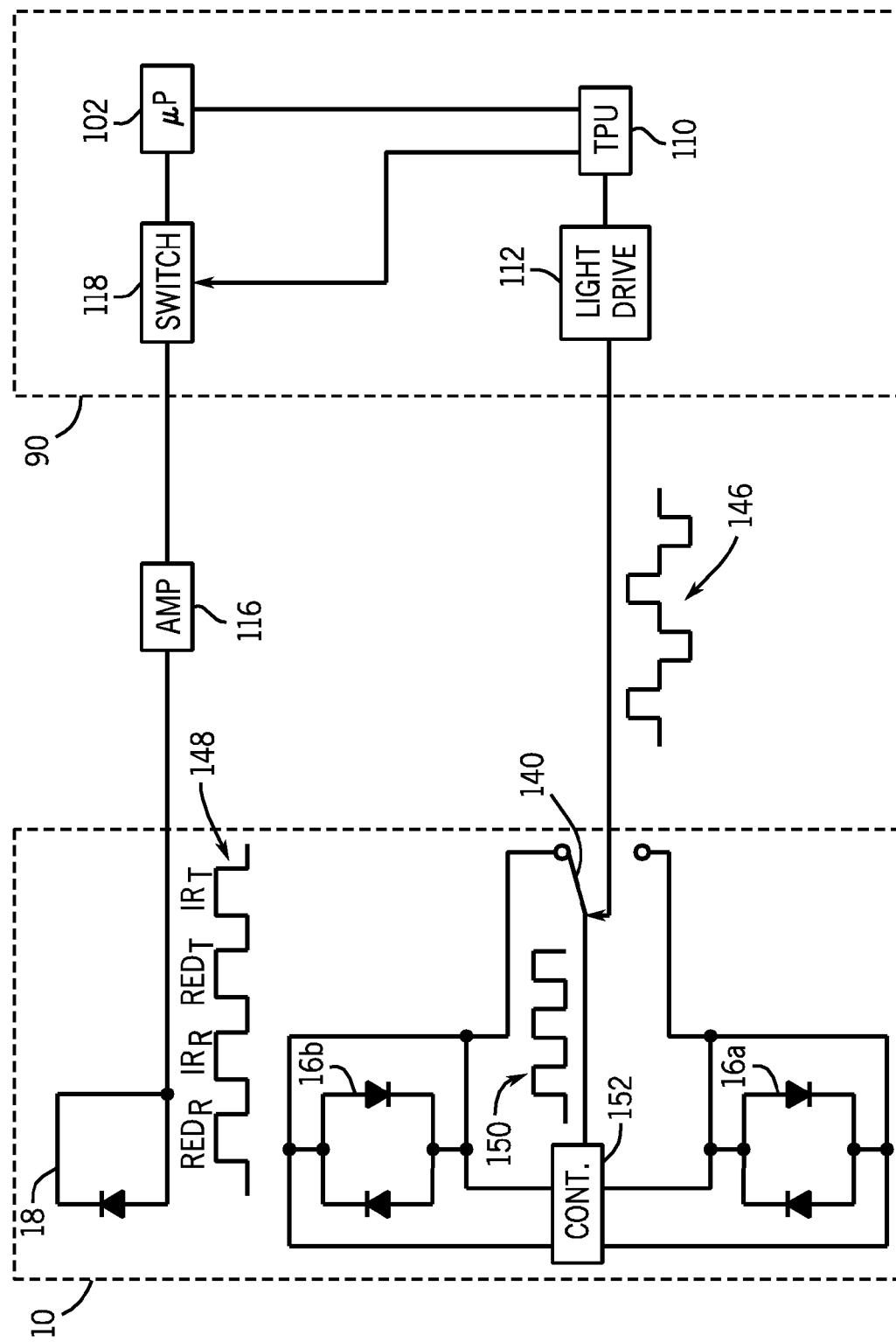
FIG. 11 is a block diagram of a dual-mode sensor with two emitters and a control on the sensor for activating each emitter according to an embodiment.

In an alternate configuration, shown in FIG. 11, an input signal 152 to the switch 140 may be controlled by a controller 152, which may be located on the sensor 10. Controller 152 may receive inputs from emitter 16a and emitter 16. Regardless of whether the control for the switch 140 is generated by the monitor 90 or the sensor 10, the red and IR diodes on each emitter 16 may further be controlled by light drive 112 and drive signal 146. The detector signal 148 includes both the red and IR components from the active emitter 16. In such a configuration, the sensor 10 may be adapted to work with off-the-shelf monitors 90, which may not need to include addition hardware or software instructions for controlling the switch between emitters 16a and 16.

Figure 12:
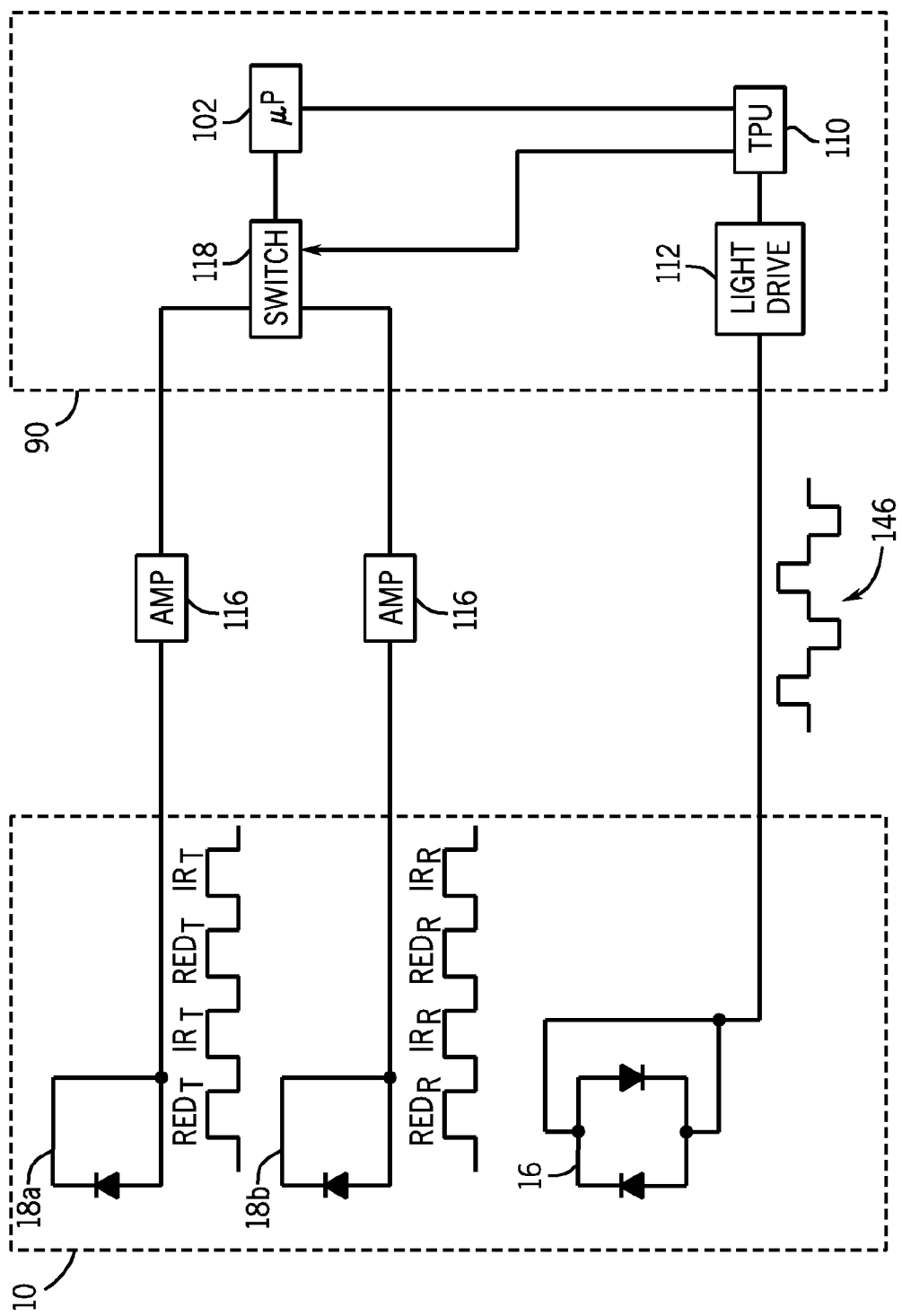
FIG. 12 is a block diagram of a dual-mode sensor with two detectors according to an embodiment.

For sensor configurations in which two detectors 18 are employed, the signals from each detector 18a and 18 may be processed within the monitor 90. As shown in FIG. 12, light drive 112 may drive a single emitter 16 with drive signal 146. When the light from the emitter 16 impinges the detectors 18a and 18, the detector 18a generates a transmission mode signal 160 that includes alternating $Red_T$ portions and $IR_T$ portions while the detector 18 generates a reflectance mode signal that includes alternating $Red_R$ portions and $IR_R$ portions. These signals may be passes through one or more amplifiers 116 and received at switch 118 for further processing by microprocessor 102. For embodiments in which the signal from one detector 18 is to be disregarded or considered inactive, for example when a particular mode is associated with low signal quality, the monitor 90 may not use the received signal from the inactive time window. Time processing unit 110 may provide time stamps to the received signals to determine the inactive and active time windows for each detector 18.

Microprocessor 102 may employ various algorithms and signal processing methods to detect and/or mitigate various types of signal artifacts associated with one or more emitter-detector pairs from transmission mode and/or reflectance mode measurements. Such signal artifacts may be the result of periodic and aperiodic movement of the sensor or sensor site within the frequency band pass of the monitor 90, which may cause time-varying photocurrents that may obscure, corrupt, or overwhelm the arterial blood pulsations. Certain types of signal processing techniques may be employed to overcome certain types of signal artifacts, which may one or more of (1) artifacts, (2) $\alpha$-artifacts, (3) $\Delta P_{tiss}$-artifact, (4) heterogeneity artifacts, and (5) boundary condition artifacts. In addition, when such signal artifacts are detected, the sensor 10 may automatically switch from the active mode (e.g., transmission or reflectance) to the inactive mode to determine if the signal artifact effects are mitigated by the switch.

1. $\eta$-artifacts

The $\eta$-artifacts (light coupling efficiency variations with time) may be related to a variation in light amplitude as a result of sensor movement relative to the tissue, the amount of light that reaches the skin, or the amount of light that strikes the photodetector. There may or may not be symmetry in the amount of the artifact between IR and red signals, depending on the source of the variation. In one embodiment, the artifact may be at least in part the result of Fresnel coupling changes, which may be related to variations in the index of refraction of the emitter, the skin, any air gap between the sensor and the sensor site, and any adhesive used. Further, as the emitter 16 and detector 18 move relative to the surface of the skin, these air gaps may open, close, or otherwise change. The resulting "Fresnel variations" in the light coupling may be as large as or larger than the magnitude of the plethysmographic signal. Accordingly, switching or arbitrating between transmission and reflectance modes may mitigate some effects of geometric changes to the sensor 10 because not all movements affect the sensor geometry symmetrically. Certain types of movements may result in larger artifacts for one mode versus another. For example, an air gap between a sensor surface and a tissue site may be localized around the transmission emitter 16a and may have less of an effect on the reflectance emitter 16.

In addition to Fresnel coupling variations, z-axis variation may be the result of changes in the geometry of the emitter 16 relative to the skin, which may result in some of the light shunting around the skin and bouncing off of another surface. The total power of the light emitted into the tissue bed may vary with the geometry of the emitter 16. Further, the geometry of the detector may also result in similar variation.

As the physical separation between the emitter 16 and the detector 18 changes, the amount of light captured by the detector varies. This is due, in part, to the varying amount of tissue the light traverses. In general, the farther apart the spacing, the less light detected. Thus, modulating the emitter-detector spacing may result in signal artifacts. In sensors 10 as provided, a switch to transmission mode, in which the spacing is farther apart, from reflectance mode, in which the spacing is relatively closer, may mitigate the effects of such modulation. In transmission mode, because the emitter and detector are farther apart, any change in distance may be a smaller percentage of the emitter-detector spacing, thus the artifact may be a smaller contribution to the signal. However, depending on the type of movement, reflectance mode configurations may have improved signal quality because of relatively higher signal amplitude. Further, anti-$\eta$-artifacts may result when the emitter tilts on the red-IR axis such that the varying emitter-to-skin spacing is not equal for both of the emitter pairs (e.g., the red LED and the IR LED for a light emitting diode pair). This may result in as much as a 180° phase shift of the red and IR plethysmographic signals if the tilting is asymmetric.

2. $\alpha$-artifacts

The $\alpha$-artifacts (e.g., blood sloshing) may be related to variation in blood flow dynamics. When subjected to acceleration or a change in acceleration, the blood in the tissue will tend to resist this change due to its mass and will move to the down-hill side of the tissue. Since the degree of light absorption within the tissue bed is a function of the amount of absorber present, the shifting blood volume results in changes in the detected light level. Venous blood dominates these changes, but is not solely responsible. Such changes may occur independently of sensor adhesion factors. For example, moving a digit up and down may cause blood volume changes related to gravity. When the movement stops, there may be a time delay (e.g., the "blood slosh" settling back into position) associated with establishing a new DC level. Instead of waiting for the signal to settle into a new DC level, these types of artifacts may be mitigated by switching modes during the time delay.

3. $\Delta P_{tiss}$-artifacts

The $\Delta P_{tiss}$-artifacts (e.g., changes in applied forces) may be the result of pressure applied to the tissue that results in localized blood redistribution to neighboring regions where the pressure is lower. Pressing or bending the tissue may result in movement of blood, movement of subcutaneous structures, changes in relative position of subcutaneous structures, changes in scattering properties of compressible portions of the tissue, changes in coupling efficiency (e.g., Fresnel coupling changes), and a varying degree of shunting. Thus, pressing on or near the sensor 10 may result in changes to the detected light levels. Also include in this category of artifacts may be the effect of sensor deformation caused by the pressure changes. For example, bending a digit at the joint may cause changes in skin color, which are related to local pressure changes. Further, such changes in tissue shape may also influence shunting that occurs at the level below the epidermis. Such changes may effect certain areas of the tissue more profoundly. For example, bending at a joint may cause localized exsanguination on the palmar side of the digit while causing an increase in redness on the side of the digit. Depending on the location of various emitters 16 and detectors 18 associated with transmission mode or reflectance mode, switching modes during a bending, pressing, or flexing motion may provide a higher quality signal.

4. Heterogeneity Artifacts

In both reflectance and transmission sensor geometries, the probing light passes through several types of tissues, depending on where the sensor is located: dermis, fat, muscle, tendon, bone, vessels, etc. Each of these different tissues uniquely affect the way in which light passes, as they each have their own scattering and absorbing properties. If movement of the sensor sites causes these structures to move relative to the sensor, the detected light levels will change. Absorption and scattering properties are wavelength dependent, thus the magnitude of these changes will not be the same in the red and IR channels. Such heterogeneity artifacts may include xy-axis sensor movement (movement of the sensor that causes the light to strike different areas of the tissue) and subcutaneous object motion (moving vessels and subcutaneous structures will modulate the light signals and may corrupt the plethysmographic signal. For sensors 10 as provided, switching modes may provide a sampling of signal quality through multiple paths. For certain patients, a particular mode may provide an optical path that is less subject to heterogeneity artifacts. For example, reflectance mode may involve an optical path that travels through fewer subcutaneous structures. Because these effects vary from patient to patient, arbitrating the signal quality between the modes at the time of application of the sensor 10 may allow the higher signal quality mode to be used.

5. Boundary Condition Artifacts

Boundary condition artifacts may encompass changes in light losses due to changes in shape of the finite boundaries of the tissue site. As the tissue bends, the surfaces may compress, stretch, fold, etc. Detected light that has traveled close to the surface will become more or less strongly attenuated as the surface geometry affects how much scatters out of the tissue. If a reflective surface is nearby, some of the light may be returned to the tissue and may or may not contribute to the overall signal, depending on where the light reenters the tissue. Secondary light modulation may occur when light exits the tissue outside of the aperture of the detector 18. Some of this light may be reflected back into the tissue to eventually reach the detector 18. If the efficiency of this process changes as a result of other artifacts, this may also influence the quality of the signal. Accordingly, switching to a second detector (e.g., detector 18) on a different area of the tissue may provide improved signal quality when a primary detector is experiencing boundary condition artifacts.

The below tables summarize the contribution of various types of motions to a particular type of artifact. Table 1 shows the artifact effects for a transmission-type digit sensor, Table 2 shows the artifact effects for a reflectance-type forehead sensor, and Table 3 shows the artifact effects for a STORM-type sensor (as provided in U.S. patent application Ser. No. 11/444,577 to Fein et al., the specification of which is incorporated by reference in its entirety herein for all purposes).

TABLE 1

Potential Effects of Different Sources of Artifact for a D-25 Digit Sensor

| Type of Motion | $\Delta\alpha$ | $\Delta\eta$ | $\Delta P_{tiss}$ | boundaries | heterogeneity |
|---|---|---|---|---|---|
| Flexing | low | high | high | high | moderate |
| Scratching | low | high | high | low | low |
| Tapping | high | high | high | moderate | moderate |
| Squeezing/Pressing | low | high | high | moderate | moderate |
| Swinging | high | low | low | low | low |
| Rubbing | low | high | high | moderate | moderate |

TABLE 2

Potential Effects of Different Sources of Artifact for a RS-10 Forehead Sensor

| Type of Motion | $\Delta\alpha$ | $\Delta\eta$ | $\Delta P_{tiss}$ | boundaries | heterogeneity |
|---|---|---|---|---|---|
| Flexing | low | high | moderate | high | moderate |
| Scratching | — | — | — | — | — |
| Tapping | — | — | — | — | — |
| Squeezing/Pressing | low | high | high | low | low |
| Swinging | moderate | low | low | low | low |
| Rubbing | low | high | high | moderate | moderate |

TABLE 3

Potential Effects of Different Sources of Artifact for a Storm 1 Sensor

| Type of Motion | $\Delta\alpha$ | $\Delta\eta$ | $\Delta P_{tiss}$ | boundaries | heterogeneity |
|---|---|---|---|---|---|
| Flexing | low | low | high | low | low |
| Scratching | low | low | high | low | low |
| Tapping | high | low | high | low | low |
| Squeezing/Pressing | low | low | high | low | low |
| Swinging | high | low | low | low | low |
| Rubbing | low | low | high | low | low |

Monitors 90 that utilize signal processing algorithms such as the STORM algorithm may be able to overcome the effects of various types of signal artifacts. STORM sensors may include sensors designed to be used where "motion provides the signal", i.e., the cardiac pulse need not be present or discernible in order for the oximeter to provide SpO$_2$ values. Instead, the red and IR waveforms resulting from the motion itself are used for determining the arterial saturation. This feature is possible for tissue beds that are well "arterialized" (a large supply of arterial blood relative to the metabolic needs of the tissue) resulting in a small arterio-venous saturation difference, as well as other signal characteristics. It has been observed that the necessary degree of arterialization correlates well to being "well perfused" at the tissue site, which itself correlates well to the tissue bed being warm. Thus by monitoring the temperature of the skin at the sensor site, and by knowing a value of temperature (programmed into the memory chip) at which the "motion-is-signal" algorithm can be utilized for the specific sensor design being used, improved reading accuracy through motion can be better accomplished.

In particular, such algorithms may be effective in overcoming boundary condition artifacts and heterogeneity-based artifacts. When such algorithms are used in conjunction with sensors 10 that are able to switch from a reflectance-type configuration to a transmission-type configuration, or vice versa, the effects of certain types of artifacts may be further reduced. For example, certain types of $\Delta P_{tiss}$ artifacts may be less profound for reflectance-type configurations relative to transmission-type configurations. As such, sensors 10 as provided may include one or more temperature sensors configured to communicate with monitor 90 and provide temperature inputs to determine whether the STORM algorithm should used to process the incoming signal from sensor 10.

Further, signal quality metrics may be employed to determine if various types of signal artifacts are present in the incoming signal. For example, a tapping motion of a digit may present a characteristic signal artifact that may be identified by the monitor 90. If such an artifact is identified, a sensor 10 may then automatically switch from a transmission mode to a reflectance mode. In other embodiments, bending or flexing of a tissue site may result in blood flow and skin discoloration changes that have a characteristic artifact effect. In such an embodiment, the sensor 10 may switch modes until the signal artifact is resolved.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A system comprising:
  a sensor comprising:
    a sensor body adapted to be applied to a patient's tissue;
    a first detector and a second detector disposed on the sensor body;
    an emitter disposed on the sensor body, wherein the emitter and the first detector are configured to operate in transmission mode and the emitter and the second detector are configured to operate in reflectance mode, and wherein the sensor is configured to alternate between transmission mode and reflectance mode such that the first detector is active when the second detector is inactive and such that the second detector is active when the first detector is inactive; and
  a monitor comprising a processor configured to:
    receive a signal from the sensor;
    determine a signal quality of the signal, wherein determining the signal quality comprises detecting a signal artifact in the signal and determining a characteristic of the signal artifact, and wherein determining the characteristic of the signal artifact comprises determining if the signal artifact comprises one or more of an η-artifact, α-artifact, $\Delta P_{tiss}$-artifact, heterogeneity artifact, or boundary condition artifact; and
    control the activation of the first detector and the second detector based on the signal quality and the characteristic of the signal artifact.

2. The system, as set forth in claim 1, wherein the sensor comprises at least one of a pulse oximetry sensor or a sensor for measuring water fraction.

3. The system, as set forth in claim 1, wherein the emitter and the first detector are spaced apart about 20 mm to about 25 mm or wherein the emitter and the second detector are spaced apart about 8 mm to about 14 mm.

4. The system, as set forth in claim 1, wherein the wherein the sensor is configured to operate in transmission mode and reflectance mode simultaneously such that the first detector and the second detector are activated simultaneously.

5. The system, as set forth in claim 4, wherein processor is configured to: receive a first signal from the first detector and a second signal from the second detector; compare a signal quality of the first signal to a signal quality of the second signal; and calculate a physiological parameter of the patient based at least in part upon the first signal or the second signal and the signal quality comparison.

6. The system, as set forth in claim 1, wherein the processor is configured to determine a type of patient motion based on the presence of one or more of the η-artifact, α-artifact, $\Delta P_{tiss}$-artifact, heterogeneity artifact, or boundary condition artifact.

7. The system, as set forth in claim 1, wherein the processor is configured to distinguish between two or more types of patient motion based at least in part upon the presence of two or more of the η-artifact, α-artifact, $\Delta P_{tiss}$-artifact, heterogeneity artifact, or boundary condition artifact.

8. The system, as set forth in claim 7, wherein the two or more types of patient motion comprise flexing, scratching, tapping, pressing, swinging, or rubbing.

9. The system, as set forth in claim 1, wherein the processor is configured to distinguish between two or more types of patient motion based at least in part upon the presence of the heterogeneity artifact and the boundary condition artifact.

10. The system, as set forth in claim 9, wherein the processor is configured to distinguish between flexing and scratching based at least in part upon the presence of heterogeneity artifact and the boundary condition artifact.

11. The system, as set forth in claim 1, wherein the processor is configured to distinguish between two or more types of patient motion based at least in part upon the presence of two or more of the η-artifact, α-artifact, $\Delta P_{tiss}$-artifact, heterogeneity artifact, or boundary condition artifact and a determination the sensor is operating in transmission mode or reflectance mode.

12. A method comprising:
  receiving a signal from a first detector disposed on a sensor body;
  determining a quality of the signal, wherein determining the quality of the signal comprises determining if the signal comprises a signal artifact and determining a characteristic of the signal artifact; and
  switching between a transmission mode and a reflectance mode based at least in part upon the characteristic of the signal artifact and a determination that the quality of the signal is below a certain threshold, wherein switching from the transmission mode to the reflectance mode comprises switching from the first detector to a second detector disposed on the sensor body.

13. The method, as set forth in claim 12, wherein determining a quality of the signal comprises determining if the signal comprises qualified pulses.

14. The method, as set forth in claim 12, wherein determining a quality of the signal comprises determining a ratio-of-ratios for the signal and determining if the ratio-of-ratios is characteristic of a high quality signal.

15. The method, as set forth in claim 12, wherein determining the characteristic of the signal artifact comprises determining if the signal artifact comprises one or more of an $\eta$-artifact, $\alpha$-artifact, $\Delta P_{tiss}$-artifact, heterogeneity artifact, or boundary condition artifact.

* * * * *